(12) United States Patent
Royo et al.

(10) Patent No.: US 6,635,778 B1
(45) Date of Patent: *Oct. 21, 2003

(54) CATALYSTS SYSTEMS FOR THE POLYMERIZATION AND COPOLYMERIZATION OF ALPHA-OLEFINS

(75) Inventors: Jose Sancho Royo, Madrid (ES); Antonio Muñoz-Escalona Lafuente, Madrid (ES); Begoña Peña Garcia, Madrid (ES); Carlos Martín Marcos, Madrid (ES)

(73) Assignee: Repsol Quimica S.A., Madrid (ES)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,347

(22) Filed: Oct. 30, 1997

(51) Int. Cl.[7] ............ C07F 7/10; B01J 31/18; C08F 4/64; C08F 10/00
(52) U.S. Cl. .......... 556/11; 502/102; 502/114; 502/160; 502/300; 585/311; 585/312; 585/702
(58) Field of Search .............. 502/102, 103, 502/114, 115, 116, 160, 300; 585/702, 311, 312; 556/11

(56) References Cited

U.S. PATENT DOCUMENTS

| | | | |
|---|---|---|---|
| 3,184,416 A | 5/1965 | Mottus | 252/429 |
| 3,440,237 A | 4/1969 | Mottus | 502/104 |
| 4,542,199 A | 9/1985 | Kaminsky et al. | 526/160 |

(List continued on next page.)

FOREIGN PATENT DOCUMENTS

| DE | 1 022 382 | 5/1963 |
|---|---|---|
| EP | 0 277 004 | 8/1988 |
| EP | 0 293 815 | 12/1988 |

(List continued on next page.)

OTHER PUBLICATIONS

J. Cihlar, et al., Influence of Water on Ethylene Polymerization Catalyzed by Titanocene Systems, *Macromol. Chem.*, vol. 179, pp. 2553–2558 (1978).

(List continued on next page.)

*Primary Examiner*—Mark Kopec
(74) *Attorney, Agent, or Firm*—Ladas & Parry

(57) ABSTRACT

Catalyst component for the polymerization of alpha-olefins of general formula (I)

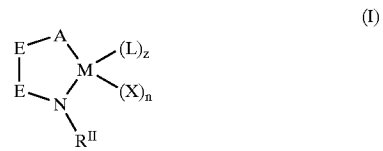

Figure 1:
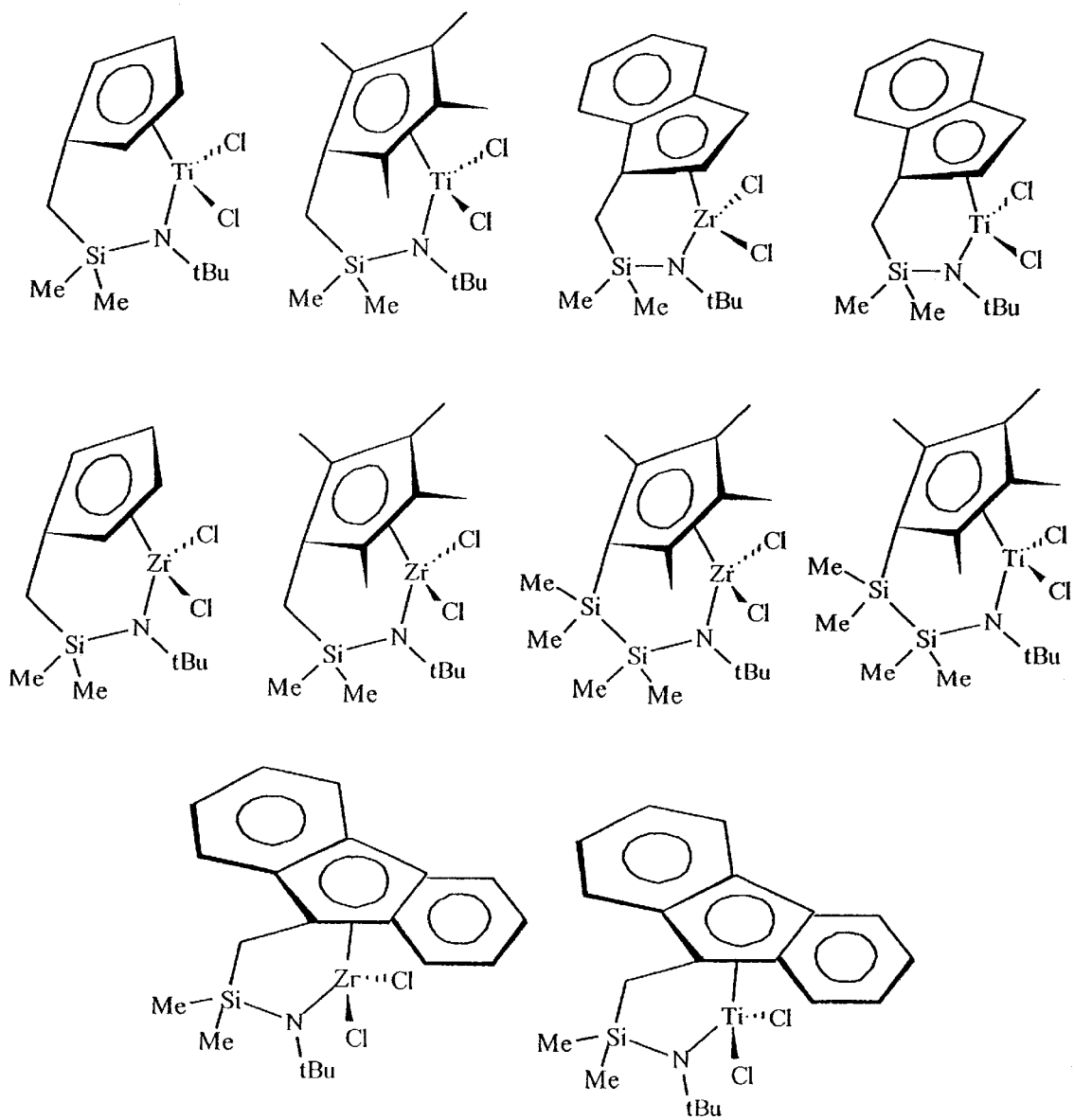

wherein:

M is a transition metal of groups 3, 4–10 of the periodic table of the elements, Each X group can be equal or different and it is hydride, halogen, alkyl, cycloalkyl, aryl, alkenyl, arylalkyl, arylalkenyl or alkylaryl with 1 to 20 carbon atoms, linear or branched. L is a neutral Lewis base A is a ring with delocalized π electrons, that directly coordinates to the transition metal M. Each E group can be equal to or different from each other and it is $BR'''$, $CR^{IV}{}_2$, $SiR'''{}_2$, $GeR'''{}_2$; at least one E is $SiR'''{}_2$. $R''$ is hydrogen, alkyl, cycloalkyl, aryl, alkenyl, arylalkyl, arylalkenyl or alkylaryl from 1 to 20 carbon atoms, linear or branched, whose hydrogens can be substituted by $SiR_3$, $GeR_3$, $OR$, $NR_2$, $OSiR_3$ or any combination of thereof. It can moreover form a condensed ring through another bond with E.

20 Claims, 1 Drawing Sheet

U.S. PATENT DOCUMENTS

| | | | |
|---|---|---|---|
| 4,939,217 A | 7/1990 | Stricklen | 526/114 |
| 5,057,475 A | 10/1991 | Canich et al. | 502/104 |
| 5,064,797 A | 11/1991 | Stricklen | 502/111 |
| 5,466,766 A | 11/1995 | Patsidis et al. | 526/129 |
| 5,627,246 A | 5/1997 | Langhauser et al. | 526/128 |
| 5,780,659 A | 7/1998 | Schmid et al. | 556/11 |
| 5,824,620 A | 10/1998 | Vega et al. | 562/117 |
| 5,846,895 A | 12/1998 | Gila et al. | 502/107 |
| 5,861,352 A | 1/1999 | Gila et al. | 502/155 |

FOREIGN PATENT DOCUMENTS

| | | |
|---|---|---|
| EP | 37 18 888 | 12/1988 |
| EP | 0 323 716 | 7/1989 |
| EP | 0 336 593 | 10/1989 |
| EP | 0 361 866 | 4/1990 |
| EP | 0 367 503 | 5/1990 |
| EP | 0 368 644 | 5/1990 |
| EP | 0 416 815 | 3/1991 |
| EP | 0 420 436 | 4/1991 |
| EP | 0 426 637 | 5/1991 |
| EP | 0 628 566 | 12/1994 |
| EP | 0 633 272 | 1/1995 |
| EP | 0 668 295 | 8/1995 |
| EP | 0 757 992 | 8/1996 |
| WO | WO 92/05203 | 4/1992 |
| WO | WO 94/03506 | 2/1994 |
| WO | WO 94/07928 | 4/1994 |

OTHER PUBLICATIONS

K. H. Reichert, et al., "Zur Kinetik der Niederdruckpolymerisation . . . ," *Die Makromolekulare Chemie*, vol. 169, pp. 163–176 (1973).

S. Collins, et al., "Polymerization of Propylene Using Supported, Chiral, ansa–Metaallocene Catalysts: Production of Polypropylene with Narrow Molecular Weight Distributions", *Macromolecules*, vol. 25, p. 1780–1785 (1992).

J. Chien, et al.,: "Olefin Copolymerizatiuon with Metallocene Catalysts. III. Supported Metallocene/Methylaluminoxane Catalyst for Olefin Copolymerization", *Journal of Polymer Science, Part A: Polymer Chemistry*, vol. 29, p. 1603–1607 (1991).

J. Chien, et al.,: "Olefin Copolymerizatiuon with Metallocene Catalysts. IV. Metallocene/Methylaluminoxane Catalyzed Olefin Terpolymerization", *Journal of Polymer Science, Part A: Polymer Chemistry*, vol. 29, p. 1609–1613 (1991).

CATALYSTS SYSTEMS FOR THE POLYMERIZATION AND COPOLYMERIZATION OF ALPHA-OLEFINS

Incorporated herein by this reference is Spanish Application No. 9602302, filed on Oct. 30, 1996. This U.S. application claims priority under 35 U.S.C. 119 to Spanish Application No. 9602302, filed on Oct. 30, 1996.

BACKGROUND

The present invention relates to new organometallic catalysts to the process for preparation thereof and their use for the polymerization and copolymerization of ethylene and alpha-olefins in industrial production plants.

There is a great variety of processes and catalysts useful for the homo- and copolymerization of olefins. Catalytic systems such as Ziegler-Natta are typically able to produce polyolefins with high molecular weight and broad distribution of molecular weight. However, for many industrial applications it is of the greatest importance to obtain polyolefins characterized by a high molecular weight, and narrow molecular weight distribution. Besides, with these Ziegler-Natta type of catalysts, to obtain copolymers with fit comonomer contents it is necessary to use high comonomer/monomer molar ratios in the feed and as a consequence the industrial process becomes enormously more expensive.

In the last years there has been the development of organometallic catalytic metallocene systems, that, combined with non-coordinative anions, alkylaluminoxanes or boron perfluorinated compounds (U.S. Pat. No. 4,542,199 and EP 426637) allow to obtain polyolefins with narrow distributions of molecular weight and high molar comonomer contents. However, the molecular weights are not as high as it would be useful to give the polymer the desired properties. Besides, these molecular weights suddenly lower when the comonomer content increases, or when the polymezation temperature rises.

In EP 416815 and EP 420436 there is the description of a new type of organometallic catalysts in which a transition metal is coordinated to a cyclopentadienyl ring and to a heteroatom. These organometallic compounds, when they are activated with alkylaluminoxanes, are able to produce ethylene polymers with high molecular weight and narrow distribution of molecular weight. They moreover own a great effectiveness in comonomer incorporation. However, when the comonomer content of the polymeric chain is increasing, the molecular weight sensibly decreases.

Therefore it is an object of the present invention to provide new compounds, useful in the (co)polymerization of alpha-olefins, in particular in the (co)polymerization of ethylene, which can produce polymers with high molecular weights. Besides, these catalysts are especially efficient in the comonomer incorporation, and produce copolymers with totally random distributions of the comonomer.

The organo metallic complexes (catalysts) disclosed in the present invention are characterized by the following general formula I:

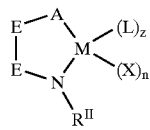

(I)

wherein:

M is a transition metal of groups 3, 4–10 of the periodic table of the elements, lanthanide or actinide, preferably titanium, zirconium or hafnium.

Each X group, equal to or different from each other, is hydrogen, halogen, alkyl, cycloalkyl, aryl, alkenyl, arylalkyl, arylalkenyl or alkylaryl with 1 to 20 carbon atoms, linear or branched, the hydrogens of these groups optionally are substituted by $SiR_3$, $GeR_3$, $OR$, $NR_2$, $OSiR_3$ groups or any combination thereof wherein R is selected from the group comprising: hydrogen, $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, branched or linear.

n is a number whose value is: 0, 1, 2 or 3, in order to fill the remaining free valences of the metal M;

L is a neutral Lewis base such as dietylether, tetrahydrofurane, dimethylaniline, aniline, triphenilphosphine, n-butylamine, etc.

z is a number whose value is: 0, 1, 2 or 3.

A is a ring with delocalized π electrons, that directly coordinates to the transition metal M. Preferably A is a cyclopentadienyl type of ring of formula $C_5R^1_4$, wherein each RW group, equal to or different from each other is hydrogen, $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, branched or linear, the hydrogens of these groups optionally are substituted by $SiR_3$, $GeR_3$, $OR$, $NR_2$, $OSiR_3$ groups or any combination thereof wherein R is above defined; $R^1$ is also selected from the group comprising $SiR_3$, $GeR_3$, $OR$, $R_2N$, $OSiR_3$ groups or any combination thereof. Two adjacent $R^1$ optionally unite in order to form a saturated or unsaturated polycyclic cyclopentadienyl ring such as indenyl, tetrahydroindenyl, fluorenyl or octahydrofluorenyl, optionally substituted with $R^1$ groups.

$R^{II}$ is hydrogen, alkyl, cycloalkyl, aryl, alkenyl, arylalkyl, arylalkenyl or alkylaryl from 1 to 20 carbon atoms, linear or branched, whose hydrogens are optionally substituted by $SiR_3$, $GeR_3$, $OR$, $NR_2$, $OSiR_3$ groups or any combination thereof wherein R is above defined; it optionally forms a condensed ring through another bond with E. Preferably $R^{II}$ is tertbutyl.

Each E group, equal to or different from each other, is $BR^{III}$, $CR^{IV}_2$, $SiR^{III}_2$, $GeR^{III}_2$; at least one E is $SiR^{III}_2$. Preferably the bridge E—E is $CR^{IV}_2$—$SiR^{III}_2$. Each $R^{III}$, equal to or different from each other, is hydrogen, alkyl, cycloalkyl, aryl, alkenyl, arylalkyl, arylalkenyl or alkylaryl with 1 to 20 carbon atoms, linear or branched, whose hydrogens optionally are substituted by $SiR_3$, $GeR_3$, $OR$, $NR_2$, $OSiR_3$ groups or any combination thereof wherein R is above defined; $R^{IV}$ has the same meaning of $R^{III}$ or it is halogen; besides two groups selected from $R^{IV}$ and $R^{III}$ belonging to different E optionally form a cyclic structure.

The catalysts component of general formula I, can be suitably prepared through reaction of a compound of general formula M'—A—E—E—$NR^{II}$—M', wherein M' is Li, Na or K, with a metal M compound, preferably of formula $MX_4$ or with an adduct of formula $MX_4 2L$ or $MX_3 3L$, where X is above defined and L preferably is a linear or cyclic ether as for example: ethylic ether, tetrahydrofurane, dimetoxyethane, etc.

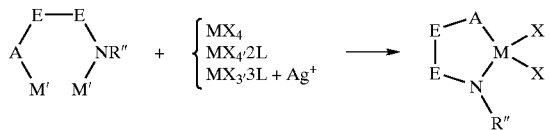

The compound of general formula M'—A—E—E—NR''—M' can be suitably prepared through reaction of HA—E—E—NR''H with two equivalents of an alkyl or aryl alkali metal salt, or with an alkali metal hydride or an alkaline metal:

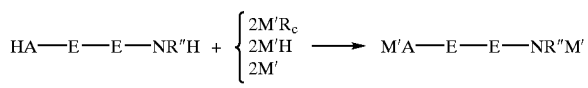

Wherein $R_c$ is $C_1$–$C_{20}$ alkyl or $C_6$–$C_{20}$ aryl.

Alternatively, alkyl magnesium salts, which are obtained in the same way, can be used, but using an alkyl magnesium halide instead of alkyl lithium.

When the bridge E—E is $SiR^{III}_2$—$CR^{IV}_2$, the compound HA—$SiR^{III}_2$—$CR^{IV}_2$—NR''H can be suitably prepared starting from a compound of general formula HA—$SiR^{III}_2$—$CR^{IV}_2$—OH or its lithium salts. The process comprises the following steps:

a) reacting a compound of formula HA—$SiR^{III}_2$—$CR^{IV}_2$—OJ wherein J is lithium or hydrogen with an alkyl- or aryl-sulphonates according to the scheme:

b) contacting the recovered product of step a) with an excess of an amine of formula $NR''H_2$

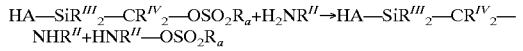

wherein $R_a$ is $C_1$–$C_{20}$ alkyl, perfluoroalkyl or $C_6$–$C_{20}$ aryl radical.

During the process for obtaining the intermediate compound of formula HA—E—E—NR''H and their alkali metal or magnesium halide salts, as well as the organometallic complexes obtained therefrom with the transition metal salts, the reaction temperature is kept between –100° C. and 95° C., preferably between –80° C. and 80° C., operating preferably under nitrogen inert atmosphere.

As non polar solvents pentane, hexane and toluene can be used; as polar aprotic solvents ethers such as diethyl ether, tetrahydrofurane or dimetoxyethane can be used.

During the whole process, both the chemical species and the solvents were protected from oxygen and humidity. The organometallic catalysts, when stored under inert atmosphere, are active in polymerization for long periods of time.

Non-limiting examples of compounds of general formula I are:

(1-tertbutylamide-2-cyclopentadienyl-1,1-dimethylsilaethanediyl)titanium dichloride
(1-tertbutylamide-2-cyclopentadienyl-1,1-dimethylsilaethanediyl))zirconium dichloride
(1-tertbutylamide-2-cyclopentadienyl-1,1-dimethylsilaethanediyl)hafnium dichloride
(1-tertbutylamide-1,1-dimethylsilaethanediyl-2-(tetramethylcyclopentadienyl)titanium dichloride
(1-tertbutylamide-1,1-dimethylsilaethanediyl-2-(tetramethylcyclopentadienyl)zirconium dichloride
(1-tertbutylamide-2-(tetramethylcyclopentadienyl)-1,1,2,2-tetramethyldisilanediyl)titanium dichloride
(1-tertbutylamide-2-(tetramethylcyclopentadienyl)-1,1,2,2-tetramethyldisilanediyl)zirconium dichloride
(1-teributylamide-2-(1-indenyl)-1,1-dimethyl-silaethanediyl)titanium dichloride
(1-tertbutylamide-2-(1-indenyl)-1,1-dimethyl-silaethanediyl)zirconium dichloride
(1-tertbutylamide-2-(1-indenyl)-1,1-dimethyl-silaethanedlyl)hafnium dichloride
(1-tertbutylamide-2-(1-indenyl)-1,1,2,2-tmethyl-silaethanediyl)titanium dichloride
(1-tertbutylamide-2-(1-indenyl)-1,1,2,2-tetra-metylsilaethanediyl)zirconium dichloride
(1-tertbutylamide-2-(1-(2methylindenyl)-1,1-dimethylsilaethanediyl)titanium dichloride
(1-tertbutylamide-2-(1-(2methylindenyl)-1,1-dimethylsilaethanediyl)zirconium dichloride
(1-tertbutylamide 2-(9-fluorenyl) 1,1)-dimethyl-silaethanediyl)titanium dichloride
(1-tertbutylamide 2-(9-fluorenyl) 1,1-dimethyl-silaethanediyl)zirconium dichloride The organometallic catalysts of formula I can be used in the polymerization and copolymerization of alpha-olefins through the addition of cocatalysts. These cocatalysts are compounds which can form non-coordinative anions, such as alkylaluminoxanes or boron perfluorinated compounds. Representative, but non-limiting, examples are methylaluminoxane, ethylaluminoxane, dimethylanilinotetrakys(pentafluorophenyl)borane, and trispentafluorophenylborane. In case boron derivatives are used, it is preferable to add to the polymerization medium little quantities of aluminium alkyls (TIBA, TEA, TMA, etc.).

The catalytic systems thus prepared are fit for the polymerization of alpha-olefins with 2 to 20 carbon atoms, in particular for the polymerization of ethylene, and for the copolymerization of ethylene with at least one alpha-olefin with 3 to 20 carbon atoms, such as propylene, 1-butene, 4-methyl-pentene, 1-hexene, etc. with dienes, with cycloalkenes and with styrene. The polymerization can be realized through a process in solution, in suspension, in gas phase or in bulk at high pressure and temperature. When using a process in suspension, hydrocarbon solvents, such as branched or linear aliphatic hydrocarbons (hexane, heptane, isobutane, etc.), cyclic hydrocarbons (benzene, toluene, xylene, etc.) or a mixture thereof are used as reaction medium. The polymerization can be realized between 1 and 4000 atmospheres and temperatures between –60 and 300° C., preferably between 40 and 220° C., and the polymerization time can vary between 20 seconds and 6 hours, according to the process.

The used concentration of the organometallic catalyst, is from $10^{-7}$ to $10^{-3}$ M, preferably form $10^{-6}$ to $10^{-4}$ M. The organoaluminum compound (for example an alumininoxane) is used in a concentration from $10^{-4}$ to $10^{-1}$ M, preferably from $10^{-3}$ to $10^2$ M. However, bigger concentrations of both components are possible as well. When an aluminoxane is used as a cocatalyst, the used Al/M molar ratio ranges from 100 to 10000, preferably between 500 and 1500. When a boron compound is used, the molar ratio varies in the range 0.5–10, preferably between 0.9–5.

The molecular weight of the obtained polymers can be controlled by varying the concentration of catalyst, cocatalyst and monomer in the polymerization medium, by varying the polymerization temperature as well as by the addition of regulators of the molecular weight such as $H_2$. When in the preparation of the catalyst only one type of cocatalyst is used, polymers with narrow distributions of the molecular weight are obtained. However, when several types of catalysts and/or cocatalysts are used, the obtained polymers have broad distribution of molecular weight, including also multimodal distributions.

The copolymerization reactions can be realized by using the same process as the one used in the homopolymerization process, but moreover by feeding the reaction medium with the suitable comonomer or comonomers. The preferred comonomer/monomer molar ratio is comprised between 0.1/1 and 5/1. In this way, copolymers with controlled content and random distribution of comonomer are obtained.

FIG. 1 shows some examples of compounds of formula I.

The following examples are described in order to better understand the invention. The materials, the chemical compounds and the conditions used in these examples are illustrative and do not limit the scope of the invention.

The average molecular weights in number, weight and distribution were determined through gel permeation chromatography GPC or SEC. The intrinsic viscosities [η] were obtained at 145° C. through viscosimetric techniques, using as a solvent trichlorobenzene with 0.05% of antioxidant in order to prevent polymer degradation.

EXAMPLE 1 a) Preparation of 2-bromo-1-tertbutylamino-1,1-dimethylsilaethane

A solution of 13.5 g (72 mmol) of 2-bromo-1-chloro-1,1-dimethylsilaethane was prepared, 21 g (288 mmol) of tertbutylamine was added dropwise, the formation of a whitish solid was immediately observed. The reaction was continued for 12 hours, then it was brought to dryness and the resulting pasty solid was extracted with hexane, the obtained solution was brought to dryness in order to obtain a yellow oil. (14.5 g, 64.7 mmol, yield: 90%). $^1$H-NMR (CDCl$_3$): 2.45(s,2H), 1.09(s,9H), 0.15(s,6H).

b) Preparation of 1-tertbutylamino-2-cyclopentadienyl-1,1-dimethylsilaethane 32.7 ml of a 2.3 M solution (75 mmol) of sodium cyclopentadienide in tetrahydrofurane was added to a solution of 11.4 g (51 mmol) of 2-bromo-1-tertbutylamino-1,1-dimethylsilaethane. The immediate formation of a pinkish solid was observed, the reaction was continued for 8 hours, then it was concentrated to dryness and it was extracted with hexane, the resulting solution was evaporated in order to give a yellow oil, that corresponds to a mixture of isomers (12.5 g, 60 mmol, yield: 80%). $^1$H-NMR (CDCl$_3$): 6.5–5.75 (m,3H), 2.95(m,2H), 1.90(m,2H), 1.20(s,9H), 0.10(s,6H).

c) Preparation of the dilithium salt of 1-tertbutylamino-2-cyclopentadienyl-1,1-dimetliylsilaethane 11.4 ml of 2.5 M solution (28.6 mmol) of butyllithium in hexane was added to a solution of 3 g (14.3 mmol) of 1-tertbutylamino-2-cyclopentadienyl-1,1-dimethyllsilaethane in ether at −78° C. It was maintained under stirring for 4 hours, at the end it was concentrated to dryness, producing a whitish solid, which was twice washed with hexane (1.7 g, 7.7 mmol, yield: 54%).

d) Preparation of (1-tertbutylamide-2-cyclopentadienyl-1,1-dimethylsilaethanediyl) titanium dichloride A suspension of 3.42 g (15.5 mmol) of the dilithium salt of 1-tertbutylamino-2-cyclopentadienyl-1,1-dimethylsilaethane in toluene was prepared and it was added to a suspension of 5.17 g (15.5 mmol) of titanium tetrachloride mixed with tetrahydrofurane in toluene at −78° C. The formation of a greenish solid was immediately observed, the reaction was left under stirring for 12 hours, the solution was filtered, obtaining a brown solution which was concentrated in order to give a brown solid, which was recrystallized in hexane (2.3 g, 7.1 mmol, yield: 46%). $^1$H-NMR (C$_6$D$_6$): 6.42 (m,3H), 5.81(m,3H), 1.82(s,2H), 1.60 (s,9H).

EXAMPLE 2 a) Preparation of (1-tertbutylamide-2-cyclopentadienyl-1,1-dimethylsilaethanediyl) zirconium dichloride A suspension of 1.46 g (6.3 mmol) of zirconium tetrachloride in toluene was prepared and a suspension of 1.4 g (6.3 mmol) of the dilithium salt of 1-tertbutylamino-2-cyclopentadienyl-1,1-dimethyllsilaethane in toluene was added. A greenish suspension immediately was formed and it was left under stirring for 12 hours. The suspension was settled, filtered and concentrated, obtaining a yellow compound: (0.74 g, 2.0 mmol, yield: 32%) $^1$H-NMR (C$_6$D$_6$): 6.22 (m,2H), 5.81(m,2H), 1.73(s,2H), 1.54 (s,9H).

EXAMPLE 3 a) Preparation of 1-tertbutylamino-2-(1-indenyl)-1,1-dimethylsilaethane

A 20 g (182 mmol) solution of indenyl lithium in tetrahydrofurane was added to a solution of 41 g (182 mmol) of 2-bromo-1-tertbutylamino-1,1-dimethylsilaethane at 0° C. After the reaction was concentrated to dryness and the residue was extracted with hexane. Finally, the solution in hexane was concentrated to the obtainment of an orange oil: 13.5 g (52 mmol, yield: 29%). $^1$H-NMR (CDCl$_3$): 7.50(m, 1H), 7.39(m,1H), 7.35(m,1H), 7.23(m,1H), 6.17(m,1H), 3.42(m,2H), 2.17(m,2H), 1.22(m,9H), 0.20(m,6H).

b) Preparation of the dilithium salt of 1-tertbutylamino-2-(1-indenyl)-1,1-dimethylsilaethane 17.3 ml of a 2.5 M (43.2 mmol) solution of butyllithium in hexane was added to a 5.6 g (21.6 mmol) solution of 1-tertbutylamino-2-(1indenyl)-1,1-dimethyllsilaethane in ether at −78° C. The butane evolution was immediately observed and, when room temperature was achieved, it was maintained under stirring for 2 hours, then it concentrates to dryness and the resulting solid was twice washed with hexane in order to give a yellowish powdery solid: 5.8 g (21 mmol, yield: 97%).

c) Preparation of [1-tertbutylamide-2-(1-indenyl)-1,1-dimethyllsilaethanediyl]titanium dichloride A suspension of 5.8 g (21 mmol) of the dilithium salt of 1-tertbutylamino-2-(1-indenyl)-1,1-dimethylsilaethane in ether was added to a suspension of 4.1 g (21.6 mmol) of titanium tetrachloride in ether at −78° C. A brown suspension immediately was formed and maintained under stirring at room temperature for 12 hours. The resulting suspension was brought to dryness and it was extracted several times with hexane, obtaining a red solution and concentrating it a dark-brown solid was formed: 2.5 g (6.7 mmol, yield: 32%). $^1$H-NMR (CDCl$_3$): 7.67(m,1H), 7.56(m,1H), 7.32(m,2H), 6.88(m,1H), 6.55(m,1H), 2.79(m,1H), 2.55(m,1H), 1.55(s, 9H), 0.62(s,3H), 0.61(s,3H). $^{13}$C-NMR (CDCl$_3$): 130.9, 128.2, 128.0, 127.3, 126.8, 126.1, 123.4, 118.4, 112.3, 63.7, 32.8, 18.4, 7.7, 6.2.

EXAMPLE 4 a) Preparation of [1-tertbutylamide-2-(1-indenyl)-1-dimethylsilaethanediyl]zirconium dichloride A suspension of 5.0 g (18.5 mmol) of the dilithium salt of 1-tertbutylamino-2-(1-indenyl)-1,1-dimethylsilaethane in ether was added to a suspension of 4.3 g (18.5 mmol) of zirconium tetrachloride in ether at −78° C. A yellowish suspension immediately forms and it was maintained under stirring at room temperature for 12 hours. The resulting suspension was brought to dryness and it was extracted several times with toluene, obtaining a yellowish solution, when concentrated it produced a yellow solid: 2.1 g (5 mmol, yield: 27%). $^1$H-NMR (CDCl$_3$): 7.60(m,2H), 7.28 (m,2H), 6.68(m,1H), 6.48(m,1H), 2.57(m,1H), 2.38(m,1H), 1.50(s,9H), 0.57(s,3H), 0.62(s,3H), 0.48(s,3H). $^{13}$C-NMR (CDCl$_3$): 128.0, 126.8, 126.3, 126.0, 125.3, 122.3, 122.0, 117.0, 103.5, 56.6, 32.6, 16.7, 7.2, 6.3.

EXAMPLE 5

To a glass reactor of 1 liter, previously dried and outgased, 600 ml of n-heptane was added. The temperature was raised to 70° C. and the solvent was stirred at 1200 rpm. When the thermal equilibrium was achieved, the medium was saturated with ethylene at a pressure of 4 bar. 10 ml of a MAO solution in toluene (1.5 M in total aluminium) and 2 bar of ethylene was added. The pressure was raised to 4 bar and 2 minutes later 0.01 mmol of the organometallic compound described in example 3 was added. The system was fed with ethylene for 15 minutes and then the polymerization was stopped by closing the ethylene flux and adding 20 ml of acidified methanol. 0.86 g of polyethylene was obtained.

EXAMPLE 6

Ethylene and 1-hexene were copolymerized. For that, the identical method as in the previous example was used, but once the solvent had been added and before pressurizing the reactor, 8 ml of dry and just-distilled 1-hexene were injected. 10 ml of a MAO solution in toluene (1.5 M in total aluminium) and 0.01 mmol of the organometallic compound described in example 3 in toluene were used. After 15 minutes of polymerization 1.4 g of polyethylene was obtained with $M_w$ 198,400 and 0.7% by mol of 1-hexene distributed at random.

EXAMPLE 7

Ethylene and 1-hexene were copolymerized. For that, the identical method as in the example 5 was used, but once the solvent had been added and before pressurizing the reactor, 25 ml of dry and just-distilled 1-hexene were injected. 10 ml of a MAO solution in toluene (1.5 M in total aluminium) and 0.01 mmol of the organometallic compound described in example 3 in toluene were used. After 15 minutes of polymerization 0.42 g of polyethylene was obtained with $M_w$ 279,000 and 1.15% by mol of 1-hexene distributed at random.

EXAMPLE 8

To a glass reactor of 1 liter, previously dried and outgased, 600 ml of n-heptane and 8 ml of dry and just-distilled 1-hexene were added. The temperature was raised to 70° C. and the solvent was stirred at 1200 rpm. When the thermal equilibrium was achieved, the medium was saturated with ethylene at a pressure of 4 bar. 10 ml of a MAO solution in toluene (1.5 M in total aluminium) and 2 bar of ethylene was added. The pressure was raised to 4 bar and 2 minutes later 0.01 mmol of the organometallic compound described in example 4 was added. The system was fed with ethylene for 15 minutes and then the polymerization was stopped by closing the ethylene flux and adding 20 ml of acidified methanol. 5.4 g of polyethylene was obtained with $M_w$ 340,796 and 0.7% by mol of 1-hexene distributed at random.

EXAMPLE 9

Ethylene and 1-hexene were copolymerized. For that, the identical method as in the example 8 was used, but once the solvent had been added and before pressurizing the reactor, 25 ml of dry and just-distilled 1-hexene were injected. 10 ml of a MAO solution in toluene (1.5 M in total aluminium) and 0.01 mmol of the organometallic compound described in example 4 in toluene were used. After 15 minutes of polymerization 5.6 g of polyethylene was obtained with $M_w$ 262,678 and 1.43% by mol of 1-hexene distributed at random.

EXAMPLE 10

To a glass reactor of 1 liter, previously dried and outgased, 600 ml of n-heptane and 8 ml of dry and just-distilled 1-hexene were added. The temperature was raised to 70° C. and the solvent was stirred at 1200 rpm. When the thermal equilibrium was achieved, the medium was saturated with ethylene at a pressure of 4 bar. 10 ml of a MAO solution in toluene (1.5 M in total aluminium) and 2 bar of ethylene was added. The pressure was raised to 4 bar and 2 minutes later 0.01 mmol of the organometallic compound described in example 2 was added. The system was fed with ethylene for 15 minutes and then the polymerization was stopped by closing the ethylene flux and adding 20 ml of acidified methanol. 1.9 g of polyethylene was obtained with $M_w$ 567066 and 0.65% by mol of 1-hexene distributed at random

EXAMPLE 11

To a glass reactor of 1 liter, previously dried and outgased, 600 ml of n-heptane and 8 ml of dry and just-distilled 1-hexene were added. The temperature was raised to 70° C. and the solvent was stirred at 1200 rpm. When the thermal equilibrium was achieved, the medium was saturated with ethylene at a pressure of 4 bar. 10 ml of a MAO solution in toluene (1.5 M in total aluminium) and 2 bar of ethylene was added. The pressure was raised to 4 bar and 2 minutes later 0.01 mmol of the organometallic compound described in example 1 was added. The system was fed with ethylene for 15 minutes and then the polymerization was stopped by closing the ethylene flux and adding 20 ml of acidified methanol. 8.3 g of polyethylene was obtained with $M_w$ 69,470 and 0.2% content of 1-hexene distributed at random

EXAMPLE 12

Ethylene and 1-hexene were copolymerized. For that, the identical method as in the example 11 was used, but once the solvent had been added and before pressurizing the reactor, 25 ml of dry and just-distilled 1-hexene were injected. 10 ml of a MAO solution in toluene (1.5 M in total aluminium) and 0.01 mmol of the organometallic compound described in example 1 in toluene were used. After 15 minutes of polymerization 9.3 g of polyethylene was obtained with $M_w$ 68,920 and 0.6% by mol of 1-hexene distributed at random.

EXAMPLE 13 a) Preparation of 1-tertbutylamino-1-dimethyl-2-tetramethylcyclopentadienylsilaethane A solution of 13 g (82 mmol) potassium tetramethylcyclopentadienide in tetrahydrofurane was added to a solution of 18.4 g (82 mmol) of 2-bromo-1-tertbutylamino-1,1-dimethylsilaethane. The immediate formation of a pinkish solid was observed, the reaction was continued for 8 hours at reflux temperature, then it was concentrated to dryness and it was extracted with hexane, the resulting solution was evaporated in order to give a orange oil (9.8 g, 37.0 mmol, yield: 45%). $^1$H-NMR (CDCl$_3$): 2.5(m,1H), 1.9(s,6H), 1.85 (s,6H), 1.12(s,9H), 1.00(m,2H), 0.10(s,6H).

b) Preparation of the dilithium salt of 1-tertbutylamino-1,1-dimethyl-2-tetramethylcyclopentadienylsilaethane 11.2 ml of 2.5 M solution (28 mmol) of butyllithium in hexane was added to a solution of 3.6 g (14 mmol) of 1-tertbutylamino-1,1-dimethyl-2-tetramethylcyclopentadienyl silaethane in ether at −78° C. It was maintained under stirring for 4 hours, at the end it was concentrated to dryness, producing a whitish solid, which was twice washed with hexane (3.3 g, 11.2 mmol, yield: 80%).

c) Preparation of [1-tertbutylamine-1,1-dimethyl-2-tetramethylcyclopentadienylsilaethane]titanium dichloride A suspension of 2.5 g (9 mmol) of the dilithium salt of 1-tertbutylamino-1,1-dimethyl-2-tetramethylcyclopentadienylsilaethane in ether was prepared and it was added to a suspension of 1.7 g (9 mmol) of titanium tetrachloride in ether at −78° C. The formation of a brownish solid was immediately observed, the reaction was left under stirring for 12 hours, the suspension was concentrated in order to give a brown oily-solid, which was recrystallized in hexane to give a red microcrystalline solid (1.3 g, 3.4 mmol, yield: 46%). $^1$H-NMR (C$_6$D$_6$): 2.30(s,2H), 2.27(s,6H), 2.22(s,6H), 1.60(s,9H), 0.50(s,6H).

EXAMPLE 14

Preparation of [1-teributylamide-1,1-dimethyl-2-tetramethylcyclopentadienylsilaethane]zirconium dichloride A suspension of 3.88 g (14 mmol) of the dilithium salt of 1-tertbutylamino-1,1-dimethyl-2-tetramethylcyclopentadienyl silaethane in ether was prepared and it was added to a suspension of 3.3 g (14 mmol) of zirconium tetrachloride in ether at −78° C. The formation of a yelowish suspension was immediately observed, the reaction was left under stirring for 12 hours, the suspension was concentrated in order to give a yelow oily-solid, which was recrystallized in hexane to give a yelow microcrystalline solid (2.3 g, 5.4 mmol, yield: 39%). $^1$H-NMR (C$_6$D$_6$): 2.20(s,6H), 2.13(s,6H), 2.12(s,2H), 1.62(s,9H), 0.42(s,6H).

What is claimed is:

1. A catalyst component for polymerization of alpha-olefins, the catalyst component having a general formula (I)

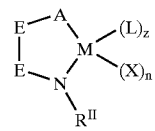

(I)

wherein:

M is a transition metal of groups 3–10 of the periodic table of the elements, lanthanide or actinide;

each X group, equal to or different from each other, is hydrogen, halogen, alkyl, cycloalkyl, aryl, alkenyl, arylalkyl, arylalkenyl or alkylaryl with 1 to 20 carbon atoms, linear or branched, the hydrogens of these groups are optionally substituted by SiR$_3$, GeR$_3$, OR, NR$_2$, OSiR$_3$ groups or any combination thereof wherein R is hydrogen, C$_1$–C$_{20}$ alkyl, C$_3$–C$_{20}$ cycloalkyl, C$_6$–C$_{20}$ aryl, C$_7$–C$_{20}$ alkenyl, C$_7$–C$_{20}$ arylalkyl, C$_7$–C$_{20}$ arylalkenyl or alkylaryl, branched or linear;

n is a number whose value is: 0, 1, 2 or 3, in order to fill remaining free valences of the metal M;

L is a neutral Lewis base;

Z is a number whose value is: 0, 1, 2 or 3;

A is a cyclopentadienyl ring of formula C$_5$R$^I_4$, wherein each R$^I$ group is equal to or different from each other and is hydrogen, C$_1$–C$_{20}$ alkyl, C$_3$–C$_{20}$ cycloalkyl, C$_6$–C$_{20}$ aryl, C$_7$–C$_{20}$ alkenyl, C$_7$–C$_{20}$ arylalkyl, C$_7$–C$_{20}$ arylalkenyl or alkylaryl, branched or linear, the hydrogens of these groups optionally are substituted by SiR$_3$, GeR$_3$, OR, NR$_2$, OSiR$_3$ groups or any combination thereof wherein R is defined in claim 1; or R$^I$ is SiR$_3$, GeR$_3$, OR, NR$_2$, an OSiR$_3$ group or any combination thereof; and wherein two adjacent R$^I$ groups optionally unite in order to form a saturated or unsaturated polycyclic cyclopentadienyl ring selected from the group consisting of tetrahydroindenyl and indenyl, optionally substituted with R$^I$ groups;

R$^{II}$ is hydrogen, alkyl, cycloalkyl, aryl, alkenyl, arylalkyl, arylalkenyl or alkylaryl from 1 to 20 carbon atoms, linear or branched, whose hydrogens optionally are substituted by SiR$_3$, GeR$_3$, OR, NR$_2$, OSiR$_3$ groups or any combination thereof wherein R is above defined; wherein R$^{II}$ optionally forms a condensed ring through another bond with E; E—E is CR$^{IV}_2$—SiR$^{III}_2$ or SiR$^{III}_2$—CR$^{IV}_2$;

each R$^{III}$, equal to or different from each other, is hydrogen, alkyl, cycloalkyl, aryl, alkenyl, arylalkyl, arylalkenyl or alkylaryl with 1 to 20 carbon atoms, linear or branched, where hydrogens optionally are substituted by SiR$_3$, GeR$_3$, OR, NR$_2$, OSiR$_3$ groups or any combination thereof wherein R is above defined; R$^{IV}$ has the same meaning of R$^{III}$ or R$^{IV}$ is halogen; wherein two groups selected from R$^{IV}$ and R$^{III}$ and belonging to different E groups optionally form a cyclic structure.

2. A catalyst component according to claim 1, wherein in general formula (I), M is selected from the group consisting of zirconium, titanium, and hafnium.

3. A catalyst component according to claim 2, wherein the bridging group E—E is CR$^{IV}_2$—SiR$^{III}_2$.

4. A catalyst component according to claim 3, wherein R$^{II}$ is tertbutyl.

5. A catalyst component as claimed in claim 2, wherein R$^{II}$ is tertbutyl.

6. A catalyst component according to claim 1, wherein the bridging group E—E is $CR^{IV}_2$—$SiR^{III}_2$.

7. A catalyst component according to claim 1, wherein $R^{II}$ is tertbutyl.

8. A catalyst component according to claim 7, wherein the bridging group E—E is $CR^{IV}_2$—$SiR^{III}_2$.

9. A catalyst component as claimed in claim 1, wherein the catalyst component is selected from the group consisting of:

(1-tertbutylamide-2-cyclopentadienyl-1,1-dimethylsilaethanediyl)titanium dichloride;
(1-tertbutylamide-2-cyclopentadienyl-1,1-dimethylsilaethanediyl)zirconium dichloride;
(1-tertbutylamide-2-cyclopentadienyl-1,1-dimethylsilaethanediyl)hafnium dichloride;
(1-tertbutylamide-1,1-dimethylsilaethanediyl-2-(tetramethylcyclopentadienyl))titanium dichloride;
(1-tertbutylamide-1,1-dimethylsilaethanediyl-2-(tetramethylcyclopentadienyl))zirconium dichloride;
(1-tertbutylamide-2-(1-indenyl)-1,1-dimethylsilaethanediyl)titanium dichloride;
(1-tertbutylamide-2-(1-indenyl)-1,1-dimethylsilaethanediyl)zirconium dichloride;
(1-tertbutylamide-2-(1-indenyl)-1,1-dimethylsilaethanediyl)hafnium dichloride;
(1-tertbutylamide-2-(1-indenyl)-1,1,2,2-tetramethylsilaethanediyl)titanium dichloride;
(1-tertbutylamide-2-(1-indenyl)-1,1,2,2-tetramethylsilaethanediyl)zirconium dichloride;
(1-tertbutylamide-2-(1-(2methylindenyl)-1,1-dimethylsilaethanediyl)titanium dichloride; and
(1-tertbutylamide-2-(1-(2methylindenyl)-1,1-dimethylsilaethanediyl)zirconium dichloride.

10. A catalyst component as claimed in claim 1, wherein the catalyst component is selected from the group consisting of:

(1-tertbutylamide-2-cyclopentadienyl-1,1-dimethylsilaethanediyl)titanium dichloride;
(1-tertbutylamide-2-cyclopentadienyl-1,1-dimethylsilaethanediyl)zirconium dichloride;
(1-tertbutylamide-2-cyclopentadienyl-1,1-dimethylsilaethanediyl)hafnium dichloride;
(1-tertbutylamide-1,1-dimethylsilaethanediyl-2-(tetramethylcyclopentadienyl))titanium dichloride;
(1-tertbutylamide-1,1-dimethylsilaethanediyl-2-(tetramethylcyclopentadienyl))zirconium dichloride;
(1-tertbutylamide-1,1-dimethylsilaethanediyl-2-(tetramethylcyclopentadienyl))hafnium dichloride;
(1-tertbutylamide-2-(1-indenyl)-1,1-dimethylsilaethanediyl)titanium dichloride;
(1-tertbutylamide-2-(1-indenyl)-1,1-dimethylsilaethanediyl)zirconium dichloride;
(1-tertbutylamide-2-(1-indenyl)-1,1-dimethylsilaethanediyl)hafnium dichloride;
(1-tertbutylamide-2-(1-indenyl)-1,1,2,2-tetramethylsilaethanediyl)titanium dichloride;
(1-tertbutylamide-2-(1-indenyl)-1,1,2,2-tetramethylsilaethanediyl)zirconium dichloride;
(1-tertbutylamide-2-(1-indenyl)-1,1,2,2-tetramethylsilaethanediyl)hafnium dichloride;
(1-tertbutylamide-2-(1-(2methylindenyl)-1,1-dimethylsilaethanediyl)titanium dichloride;
(1-tertbutylamide-2-(1-(2methylindenyl)-1,1-dimethylsilaethanediyl)zirconium dichloride; and
(1-tertbutylamide-2-(1-(2methylindenyl)-1,1-dimethylsilaethanediyl)hafnium dichloride.

11. A catalyst system comprising a cocatalyst selected from the group consisting of: alkylaluminoxane, modified aluminoxane, and boron compounds, wherein the catalyst system further comprises a catalyst component according to claim 1.

12. A catalyst system according to claim 11 wherein the cocatalyst is selected from the group consisting of: methylaluminoxane, ethylaluminoxane, N,N-dimethylanilinium tetrakys(pentafluorophenyl)borate, and trispentafluorophenylborane.

13. A process for obtaining polyolefins in solution, in suspension, in gas phase at low or high pressures and temperatures or in mass at high pressure and high or low temperatures, wherein the catalyst system according to claim 11 is used.

14. A process for obtaining polyolefins according to claim 13, wherein polymerization temperature varies between −60° C. and 300° C., pressure varies between 1 and 4000 atmospheres, transition metal concentration varies between $10^{-7}$ and $10^{-3}$ M, the cocatalyst is an aluminium organocomplex, and cocatalyst/transition metal molar ratio varies between 10 and 10000.

15. A process for obtaining polyolefins according to claim 14, wherein the polymerization temperature varies between −40° C. and 220° C., the transition metal concentration varies between $10^{-6}$ and $10^{-4}$ M, and the cocatalyst/transition metal molar ratio varies between 500 and 1500.

16. A process for obtaining polyolefins according to claim 13, wherein polymerization temperature varies between −60° C. and 300° C., pressure varies between 1 and 4000 atmospheres, transition metal molar concentration varies between $10^{-7}$ and $10^{-3}$, the cocatalyst is a boron compound, and cocatalyst/transition metal molar ratio varies between 0.5 and 10.

17. A process for obtaining polyolefins according to claim 16, wherein the polymerization temperature varies between −40° C. and 220° C., the transition metal concentration varies between $10^{-6}$ and $10^{-4}$ M, and the cocatalyst/transition metal molar ratio varies between 0.9 and 5.

18. A process for obtaining polyolefins according to claim 13, wherein ethylene monomer is used.

19. A process for obtaining ethylene copolymers according to claim 13, wherein comonomer is selected from the group consisting of: propene, 1-butene, 1-hexene, 1-octene, 1-hexadecene, 4-methyl-pentene, hexadiene, styrene, and mixtures thereof.

20. A process for obtaining the catalyst component as claimed in claim 1, wherein the catalyst component has the following formula:

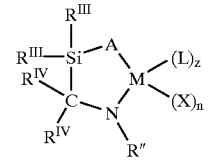

wherein A, E, M, L, X, n, z, $R^{II}$, $R^{III}$ and $R^{IV}$ are defined in claim 1, wherein the process comprises the following steps:

(a) reacting a compound of formula HA—$SiR^{III}_2$—$CR^{IV}_2$—OJ wherein J is lithium or hydrogen with an alkyl- or aryl-sulphonate according to the scheme:

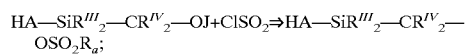

(b) contacting the recovered product of step (a) with an excess of an amine of formula $NR^{II}H_2$:

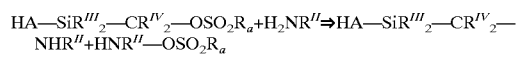

wherein $R_a$ is $C_1$–$C_{20}$ alkyl, perfluoroalkyl, or $C_6$–$C_{20}$ aryl radical;

(c) treating the compound of formula HA—SiR$^{III}_2$—CR$^{IV}_2$—NHR$''$ with two equivalents of an alkyl or aryl alkali metal salt, or with an alkali metal hydride or an alkali metal according to the following scheme:

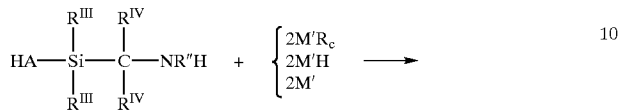

-continued

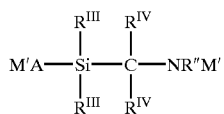

wherein $R_c$ is $C_1$–$C_{20}$ alkyl or $C_6$–$C_{20}$ aryl and M' is Li, Na, or K; and (d) contacting the compound of formula M'A—SiR$^{III}_2$—CR$^{IV}_2$—NR$''$M' with a metal M compound of formula MX$_4$ or with an adduct of formula MX$_4$.2L, or MX$_3$.3L, wherein L is a linear or cyclic ether.

* * * * *